United States Patent [19]

Mohler et al.

[11] 4,108,995
[45] Aug. 22, 1978

[54] HYDROXYHEXYL-ALKYLXANTHINES AND PHARMACEUTICAL COMPOSITIONS CONTAINING HYDROXYHEXYL-ALKYLXANTHINES

[75] Inventors: Werner Mohler, Hofheim; Manfred Jayme, Rüsselsheim; Heinz-Joachim Hinze, Wiesbaden; Jaromir Komarek, Wiesbaden; Mario Reiser, Wiesbaden; Alfons Söder, Frankfurt-Schwanheim, all of Germany

[73] Assignee: Hoechst Aktiengesellschaft

[21] Appl. No.: 485,869

[22] Filed: Jul. 5, 1974

[30] Foreign Application Priority Data

Jul. 11, 1973 [DE] Fed. Rep. of Germany ....... 2335170

[51] Int. Cl.$^2$ .................... A61K 31/52; C07D 473/06
[52] U.S. Cl. ..................................... 424/253; 544/267
[58] Field of Search .......................... 260/256; 424/253

[56] References Cited

U.S. PATENT DOCUMENTS 2,517,410  8/1950  Papesch ............................ 260/256
2,756,229  7/1956  Stoll et al. ........................ 260/256

FOREIGN PATENT DOCUMENTS 1,211,333  10/1959  France.
926,788  4/1955  Fed. Rep. of Germany ........... 260/256

OTHER PUBLICATIONS

Archiv der Pharmazie, vol. 299 (1966), pp. 448 to 456.
Dissertationes Pharmaceuticae et Pharmacologicae, vol. XX, pp. 502–510, 1968.

*Primary Examiner*—Paul M. Coughlan, Jr.
*Attorney, Agent, or Firm*—Berman, Aisenberg & Platt

[57] ABSTRACT

Compound of the formula

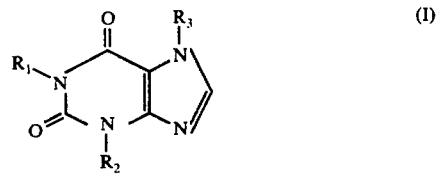

wherein one of the groups $R_1$, $R_2$ and $R_3$ is a hydroxyalkyl group containing from 4 to 8 carbon atoms, one of the other two, which may be the same or different, is an alkyl group containing from 2 to 12 carbon atoms and the third one is an alkyl group containing from 1 to 12 carbon atoms or a hydrogen atom, $R_2$ however being an alkyl or hydroxyalkyl group, at least one of the groups $R_1$, $R_2$ and $R_3$ containing at least 5 carbon atoms, a process for their preparation and a pharmaceutical composition containing said compounds.

21 Claims, No Drawings

HYDROXYHEXYL-ALKYLXANTHINES AND PHARMACEUTICAL COMPOSITIONS CONTAINING HYDROXYHEXYL-ALKYLXANTHINES

This invention relates to pharmaceutical compositions for use in the treatment of diseases involving insufficiency of cerebral blood flow.

The number of hydrophylising groups per alkyl group in these compounds is generally from 1 up to the number of carbon atoms in the particular alkyl group, preferably from 1 to 4 carbon atoms. Compounds having a hydroxyl substituent on a carbon atom adjacent to a ring nitrogen atom are unstable. The only compounds which have been specifically disclosed, however, are those in which each hydroxyalkyl group has 2 or 3 carbon atoms, one hydroxyl group is in the β-position to the revelant ring nitrogen atom (but the hydroxyalkyl group may contain an additional hydroxyl group) and all those alkyl groups which are not hydroxylated are methyl groups. The only monohydroxyalkyl compounds which have been specifically disclosed are the monohydroxyalkyl derivatives of theobromine and theophylline.

Other physiologically active xanthines substituted with three alkyl groups in the 1-, 3- and 7-position are known in which 1,2 or all 3 of the alkyl groups are monohydroxylated and contain 3 or 4 carbon atoms and the remaining alkyl substituents are unsubstituted. One such compound, for example, is 7-(β-hydroxypropyl)-1,3-diethylxanthine. Where these mixtures have been described, however, no specific hydroxyalkyl compounds have been disclosed nor has the preferred position of the hydroxyl groups been specified.

According to the present invention we now provide pharmaceutical compositions comprising as active ingredient a compound of formula

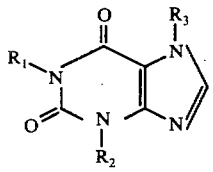

(I)

wherein one of the groups $R_1$, $R_2$ and $R_3$ is a hydroxyalkyl group containing from 4 to 8 carbon atoms, one of the other two, which may be the same or different, is a straight-chain or branched alkyl group containing from 2 to 12 carbon atoms, and the third one is a straight-chain or branched alkyl group containing from 1 to 12. carbon atoms or a hydrogen atom at least one of the groups $R_1$, $R_2$ and $R_3$ containing at least 5 carbon atoms, and $R_2$ being a substituent other than hydrogen, or a physiologically acceptable acid addition salt thereof in association with a pharmaceutical carrier or excipient.

The compounds of general formula I as hereinbefore defined and physiologically acceptable acid addition salts thereof are also new and constitute a further feature of the invention.

In general the compositions according to the invention act to improve cerebral blood flow and the effect is usually of long duration. In comparison the known short-chain hydroxyalkyl derivatives of theophylline and theobromine do not appear to have a similar activity. The pharmacological activity spectrum of the new compounds is otherwise substantially the same as that of the known short-chain hydroxyalkyl derivatives of theophylline and theobromine. The new compounds also have the effect of generally improving the flow properties of blood and are therefore useful in the treatment of arterial blood supply disturbances. Their toxicity is low.

Preferred compounds of general formula I according to the invention by virtue of their particularly favourable pharmacological activity are those wherein the hydroxyl group in the hydroxyalkyl group is in the ω-, (ω-1)- or (ω-2)- position, and wherein the hydroxyalkyl group is unbranched and in the 1- or 7-position. Compounds in which the alkyl groups contain more than 2 carbon atoms are also preferred.

The following are specific examples of the new compounds according to the invention:

1-ethyl-3-methyl-7-(5-hydroxyhexyl)-xanthine,
1-propyl-3-methyl-7-(5-hydroxyhexyl)-xanthine,
1-n-butyl-3-methyl-7-(5-hydroxyhexyl)-xanthine,
1-isobutyl-3-methyl-7-(5-hydroxyhexyl)-xanthine,
1-pentyl-3-methyl-7-(5-hydroxyhexyl)-xanthine,
1-hexyl-3-methyl-7-(5-hydroxyhexyl)-xanthine,
1-decyl-3-methyl-7-(5-hydroxyhexyl)-xanthine,
1-(5-hydroxyhexyl)-3-methyl-7-ethyl-xanthine,
1-(5-hydroxyhexyl)-3-methyl-7-propyl-xanthine,
1-(5-hydroxyhexyl)-3-methyl-7-n-butyl-xanthine,
1-(5-hydroxyhexyl)-3-methyl-7-isobutyl-xanthine,
1-(5-hydroxyhexyl)-3-methyl-7-hexyl-xanthine,
1-(5-hydroxyhexyl)-3-methyl-7-decyl-xanthine,
1-(5-hydroxyhexyl)-3-butyl-7-propyl-xanthine;
1-hexyl-3-(5-hydroxyhexyl)-7-methylxanthine and the corresponding (2-methyl-3-hydroxybutyl)-, hydroxyheptyl and hydroxybutyl- compounds (the latter in so far as they have an alkyl substituent with at least 5 carbon atoms), for example 1-(2-methyl-3-hydroxybutyl)-3-methyl-7-propyl-xanthine and 1-propyl-3-methyl-7-(2-methyl-3-hydroxybutyl)-xanthine; the 1-alkyl-3-methyl-7-(6-hydroxyhexyl)-xanthines and 1-(6-hydroxyhexyl)-3-methyl-7-alkyl-xanthines, for example 1-(6-hydroxyhexyl)-3-methyl-7-ethyl-xanthine, and 1-(6-hydroxyhexyl)-3-methyl-7-propyl-xanthine; and the corresponding hydroxyheptyl and hydroxybutyl compounds (the latter insofar as they have an alkyl substituent with at least 5 carbon atoms).

The pharmaceutical compositions according to the invention may be presented in a form suitable for oral, rectal or parenteral administration. They may be thus administered in solid form or in solution. Many of the xanthine derivatives according to the invention are sufficiently soluble in sterile water to be made up into injectable solutions for parenteral administration.

Suitable forms for administration include for example solutions, emulsions, tablets, coated tablets, suppositories, granulates and sustained release forms. These may be prepared in known manner using the usual auxiliary agents such as excipients, disintegrants, binders, coating substances, swelling substances, lubricants, flavourings, sweeteners, substances for obtaining a sustained release effect and solubilising agents. Suitable auxiliary substances include for example lactose, mannitol, talcum, milk protein, starch, gelatine, cellulose and its derivatives such as methyl cellulose, hydroxyethyl cellulose and suitable swelling and non-swelling copolymers. The disintegration of the composition and hence also the release of active ingredients can be influenced by means of extenders which may be used in large or small quantities.

Advantageously the new compositions according to the invention are presented in the form of dosage units, each dosage unit being adapted to supply a fixed quantity of active ingredient, preferably up to 400 mg of active ingredient.

If desired the new compositions may additionally contain a further active ingredient, for examples a vitamin.

The invention also comprises a process for the preparation of compounds of general formula I wherein (a) an alkali metal salt of a compound of formula (I), but which contains instead of the hydroxyalkyl group and if desired additionally as a radical $R_1$, $R_2$ or $R_3$ a hydrogen atom, is reacted in conventional manner with one mol of a hydroxy alkyl halide or (b) an alkali metal salt of a compound of the formula I, but in which at least one of the radicals $R_1$ and $R_3$ is a hydrogen atom and one of the radicals $R_1$, $R_2$ and $R_3$ is a hydroxy alkyl radical, is reacted in solution with an alkylating agent or (c) a compound of formula (I), but in which one of the radicals $R_1$, $R_2$ or $R_3$ is a halogen alkyl radical instead of the hydroxy alkyl radical, is reacted with an alkali metal salt of a lower fatty acid having 1 to 6 carbon atoms to obtain the corresponding carboxylic acid ester, which is hydrolytically split to obtain the products of the invention or (d) wherein a compound of formula (I) having an oxygen atom in the place of the hydroxy group is reduced whereby the carbonyl group is transformed to a hydroxyl group or (e) wherein water is added to a compound of formula (I) having an ($\omega$-1)-alkenyl group in the place of the hydroxy alkyl group.

The $\omega$-hydroxyalkyl compounds may be prepared according to embodiment (a), for example, by reacting an alkali metal salt of a compound of formula I (wherein one of $R_1$, $R_2$ and $R_3$ represents a hydrogen atom, one of the other two, which may be the same or different, is a straight-chain or branched alkyl group containing from 2 to 12 carbon atoms and the third one is a straight-chain or branched alkyl group containing from 1 to 12 carbon atoms or a hydrogen atom) with an $\omega$-hydroxyalkyl halide containing 4 to 8 carbon atoms. The alkali metal salt may be prepared by addition of an alkali, in the presence of a solvent, for example in an alcohol with 1 to 3 carbon atoms, e.g. methanol, ethanol or isopropanol, or in an aprotic solvent such as formamide, dimethylformamide or dimethyl sulphoxide. The alkali may in particular be in the form of aqueous sodium hydroxide solution, solid sodium hydroxide or a sodium alcoholate or a corresponding potassium compound. The reaction is preferably carried out by adding the $\omega$-hydroxyalkyl halide to the alkali metal salt and heating the solution.

A method of preparation according to embodiment (b) of the invention comprises reacting an alkali metal salt of a hydroxyalkyl-xanthine having hydrogen atoms in the 1- and/or 7-positions with suitable alkylating agents, for example straight-chain or branched alkyl halides, e.g. alkyl chlorides, bromides and iodides, or dialkylsulphates, preferably in aqueous-organic solution. The aqueous-organic solution consists of a mixture of water with organic solvents being miscible with water, e.g. the above-mentioned alcohols and aprotic solvents.

A method of preparation of the new compounds according to embodiment (c) of the invention comprises reacting a compound of formula I (wherein one of the groups $R_1$, $R_2$ and $R_3$ represents a haloalkyl group containing from 4 to 8 carbon atoms, one of the other two, which may be the same or different, is a straight-chain or branched alkyl group containing from 2 to 12 carbon atoms and the third one is a straight-chain or branched alkyl group containing from 1 to 12 carbon atoms or a hydrogen atom, at least one of the groups $R_1$, $R_2$ and $R_3$ containing at least 5 carbon atoms and $R_2$ being a substituent other than hydrogen) with an alkali metal salt of a carboxylic acid containing 1 to 6 carbon atoms, whereby a carboxylic acid ester is produced, and subsequently hydrolysing this ester. The hydrolysis is preferably effected in the presence of an acid, for example dilute sulphuric acid, advantageously at temperatures from 10° to 100° C. This process gives almost quantitative yields of the hydroxyalkyl-xanthine compounds according to the invention.

The reduction according to embodiment (d) is applied with particular advantage to compounds which have the oxo-atom in ($\omega$-1) or ($\omega$-2)-position, and may be effected by means of conventional reducing agents which bring about the conversion of an oxo-group into a hydroxyl group. The oxo-alkyl-xanthines used as starting material for this process may be prepared as described in U.S. patent application Ser. No. 479,434, filed June 14, 1974, now abandoned (corresponding to German Application No. P 23 30 742.8). The reduction is conveniently effected by means of a complex borohydride, an aluminum alcoholate, magnesium or sodium in an alcohol with 1 to 3 carbon atoms, preferably methanol, ethanol or isopropanol, with sodium amalgam with zinc in aqueous potassium hydroxide, lithium aluminum hydride or by catalytic hydrogenation. Such hydrogenation is preferably effected in the presence of a catalyst comprising palladium on charcoal, Raney nickel, copper/chromium oxide or metallic platinum prepared from platinum oxide and finely dispersed in the solution. The reduction of ketoalkyldialkyl-xanthines with sodium borohydride in aqueous and/or alcoholic solution has been found to be particularly advantageous.

The reaction according to embodiment (e) is advantageously carried out in an aqueous solution or suspension and advisably in the presence of an acid, such as a mineral acid, e.g. sulphuric acid, a hydrogen halide, nitric acid, phosphoric acid, a sulphonic acid such as trifluoromethyl sulphonic acid or an ion exchanger having —$SO_3H$— groups. If desired this reaction may be carried out in the presence of an organic solvent being inert against dilute acids, such as 1,4-dioxane, benzene or toluene. This embodiment is in general carried out at a temperature in the range from 40° to 150° C, preferably from 60° to 120° C. The termination of the reaction may be determined by chromatographic methods. The desired final products may be obtained from the aqueous phase by extraction with suitable agents, e.g. chlorinated hydrocarbons such as methylene chloride or chloroform. Where in addition to the aqueous phase an organic phase is present, further portions of the desired products may be obtained by distilling off the solvent, if desired under reduced pressure.

A further subject of the invention is compounds of formula I which, in place of the hydroxyalkyl group, have an ($\omega$-1)-alkenyl group. Thus, in these compounds one of the groups $R_1$, $R_2$ and $R_3$ is an ($\omega$-1)-alkenyl group having from 4 to 8 carbon atoms in which the double bond is separated from the xanthine nucleus by at least one carbon atom, one of the other two radicals $R_1$ to $R_3$, which may be equal or different, is a straight-chain or branched alkyl group of 2 to 12 carbon atoms and the third one is a straight-chain or branched alkyl group containing 1 to 12 carbon atoms or hydrogen with the proviso that $R_2$ is said alkenyl group or alkyl. These compounds may be used as starting materials in the reaction of embodiment (e). Suitable compounds are e.g. 1-(5-hexenyl)-3-methyl-7-ethylxanthine, 1-(5-hexenyl)-3-methyl-7-propylxanthine, 1-(5-hexenyl)-3-methyl-7-butyl-xanthine, 1-(5-hexenyl)-3-methyl-7-isobutylxanthine, 1-(5-hexenyl)-3-methyl-7-decylxanthine, 1-propyl-3-methyl-7-(5-hexenyl)-xanthine, 1-isobutyl-3-methyl-7-(5-hexenyl)-xanthine, 1-pentyl-3-methyl-7-(5-hexenyl)-xanthine, 1-hexyl-3-methyl-7-(5-hexenyl)-xanthine.

The following Examples serve to illustrate the preparation of the new compounds according to the invention.

EXAMPLE 1

3.25 g of sodium borohydride are added under stirring to a suspension of 70 g of 1-(5-oxohexyl)-3-methyl-7-propyl-xanthine in 500 g of water. After stirring for 1½ hours at ambient temperature the excess of sodium borohydride is decomposed with 2.5 ml of crystalline acetic acid. The solution is made alkaline and extracted with methylene chloride. The methylene chloride solution is evaporated and the residue is dissolved in a small quantity of methanol. 1-(5-Hydroxyhexyl)-3-methyl-7-propyl-xanthine having a melting point of 76° to 77° C is precipitated with diisopropyl ether in a yield of about 90%. The solubility in water, ethanol and dimethylsulfoxide is above 10%, that in 1,2-propylene-glycol between 1 and 10%.

EXAMPLE 2

1-(5-Hydroxyhexyl)-3-methyl-7-ethyl-xanthine having a melting point of 87° C is obtained in 95% yield from 70 g of 1-(oxohexyl)-3-methyl-7-ethylxanthine, 500 g of water and 3.4 g of sodium borohydride analogously to Example 1. The solubility in water, ethanol and dimethylsulfoxide is above 10%, that in 1,2-propylene-glycol between 1 and 10%.

EXAMPLE 3

1-(5-Hydroxyhexyl)-3-methyl-7-n-butylxanthine is obtained in almost quantitative yield from 30 g of 1-(5-oxohexyl)-3-methyl-7-n-butyl-xanthine, 200 g of water and 10 g of sodium borohydride analogously to Example 1. After distillation in vacuo (208° C / 0.1 mm Hg) and recrystallisation from diisopropyl ether the product has a melting point of 56° to 57° C.

EXAMPLE 4

A crude product is obtained from 30 g of 1-(5-oxohexyl)-3-methyl-7-isobutyl-xanthine, 250 g of water and 5 g of sodium borohydride in a quantitative yield analogously to Example 1. After distillation in vacuo (210° C / 0.2 mm Hg) and recrystallisation from diisopropyl ether, 1-(5-hydroxyhexyl)-3-methyl-7-isobutyl-xanthine having a melting point of 54° to 55° C is obtained.

EXAMPLE 5

A crude product is obtained in a quantitative yield from 30.6 g 1-n-propyl-3-methyl-7-(5-oxohexyl)-xanthine, 250 g of water and 1.8 g of sodium borohydride analogously to Example 1. After recrystallisation from 700 ml of diisopropyl ether, 1-n-propyl-3-methyl-7-(5-hydroxyhexyl)-xanthine having a melting point of 53° C is obtained.

EXAMPLE 6

31.9 g of a crude product are obtained from 31.6 g of 1-isobutyl-3-methyl-7-(5-oxohexyl)-xanthine, 250 g of water and 3.5 g of sodium borohydride analogously to Example 1. After recrystallisation from 400 ml of diisopropyl ether, 1-isobutyl-3-methyl-7-(5-hydroxyhexyl)-xanthine having a melting point of 62° to 63° C is obtained in a yield of about 80%.

EXAMPLE 7

25 g of 1-n-hexyl-3-methyl-7-(5-oxohexyl)-xanthine, 100 ml of methanol and 1.0 g sodium borohydride are stirred at ambient temperature for 30 minutes. The mixture is then acidified with crystalline acetic acid to a pH-value of 5. The alcohol is evaporated and the residue is dissolved in 200 ml of methylene chloride and washed with 2N sodium hydroxide solution and with water. After evaporation of the methylene chloride, the product is recrystallised from 250 ml of diisopropyl ether. The 1-n-hexyl-3-methyl-7-(5-hydroxyhexyl)-xanthine obtained (88% of theory) has a melting point of 68° to 69° C.

EXAMPLE 8

24.5 g of a crude product are obtained from 25 g of 1-(5-oxohexyl)-3-methyl-7-n-decylxanthine, 200 ml of methanol and 0.9 g of sodium borohydride analogously to Example 7. This crude product is recrystallised from 100 ml of diisopropyl ether. The 1-(5-hydroxyhexyl)-3-methyl-7-n-decyl-xanthine obtained (85% of theory) has a melting point of 37° to 38° C.

EXAMPLE 9

15 g of 3-methyl-7-ethyl-xanthine are dissolved in a mixture of 20 ml of water and 350 ml of methanol by adding 3.4 g of solid sodium hydroxide and heating. 14.5 g of 6-bromohexanol-(1) are then added. After boiling overnight, the alcohol is distilled off and the solution is extracted with methylene chloride at a pH-value of 10. The extract is removed. At a pH-value of 7.2 the mixture is again extracted with methylene chloride and the solvent is distilled off. The residue is recrystallised from a small quantity of isopropanol. The 1-(6-hydroxyhexyl)-3-methyl-7-ethyl-xanthine having a melting point of 93° C is recrystallized from a small quantity of acetone on the addition of cyclohexane (Yield: about 80%).

EXAMPLE 10

20 g of 3-methyl-7-propyl-xanthine, 4.2 g of sodium hydroxide in 20 ml of water and 17.4 of 6-bromohexanol-(1) in 350 ml of methanol are reacted together analogously to Example 9. After removal of the methanol the desired product is extracted with methylene chloride at a pH-value of 10. The crude product is recrystallised from a mixture of methanol and water (volume ratio 1:1). 1-(6-hydroxyhexyl)-3-methyl-7-propylxanthine having a melting point of 68° to 70° C is obtained in a yield of about 85%.

EXAMPLE 11

10.3 g of 1-bromohexene-(5) are reacted at 120° C with 24.4 g of the sodium salt of 3-methyl-7-butyl-xanthine in 200 ml of dimethylformamide, while stirring, until the termination of the reaction is determined from a thin layer chromatogram, i.e. after about 6 to 8 hours.

The solvent is then distilled off under reduced pressure. The residue is dissolved at 20° C in 120 ml of methylene chloride, separated from the undissolved sodium bromide and purified in a column of neutral alumina in order to remove small amounts of dark contaminations.

The methylene chloride is distilled off from the solution obtained and the 1-(5-hexenyl)-3-methyl-7-butyl-xanthine is isolated.

3.0 g of 1-(5-hexenyl)-3-methyl-7-butyl-xanthine are boiled with 25 ml of 1-normal sulfuric acid for 24 hours. After termination of the reaction the product is neutralized and extracted with methylene chloride from which 1-(5-hydroxyhexyl)-3-methyl-7-butyl-xanthine is obtained in colourless crystals having after recrystallization from methanol a melting point of 56° to 57° C. The yield is 3.0 g (93% of the theory).

EXAMPLES 12 to 19

In a manner analogous to that described in Example 11 the following compounds have been prepared:

Table 1

| | Melting point °C |
|---|---|
| 12) 1-(5-hydroxyhexyl)-3-methyl-7-propyl-xanthine | 76–77 |
| 13) 1-propyl-3-methyl-7-(5-hydroxyhexyl)-xanthine | 53 |
| 14) 1-pentyl-3-methyl-7-(5-hydroxyhexyl-xanthine | 65–67 |
| 15) 1-(5-hydroxyhexyl)-3-methyl-7-ethyl-xanthine | 87 |
| 16) 1-(5-hydroxyhexyl)-3-methyl-7-isobutyl-xanthine | 54–55 |
| 17) 1-(5-hydroxyhexyl)-3-methyl-7-decyl-xanthine | 37–38 |
| 18) 1-isobutyl-3-methyl-7-(5-hydroxyhexyl)-xanthine | 62–63 |
| 19) 1-hexyl-3-methyl-7-(5-hydroxyhexyl)-xanthine | 68–69 |

It is not intended that the examples given herein should be construed to limit the invention thereto, but rather they are submitted to illustrate some of the specific embodiments of the invention. Resort may be had to various modifications and variations of the present invention without departing from the spirit of the discovery or the scope of the appended claims.

What we claim is:

1. A physiologically-acceptable and pharmacologically-active cerebral-blood-flow-improving compound of the formula

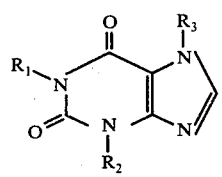

wherein
one of $R_1$, $R_2$ and $R_3$ is 4-, 5- or 6- hydroxyhexyl;
one of $R_1$, $R_2$ and $R_3$ is alkyl having from 2 to 12 carbon atoms; and
one of $R_1$, $R_2$ and $R_3$ is a hydrogen atom (-H) or alkyl having from 1 to 12 carbon atoms; and
$R_2$ being alkyl or hydroxyhexyl; or a physiologically-acceptable acid-addition salt of such compound.

2. A compound according to claim 1 which is 1-(5-hydroxyhexyl)-3-methyl-7-(ethyl, propyl, n-butyl, isobutyl or n-decyl)xanthine, 1-(6-hydroxyhexyl)-3-methyl-7-(ethyl or propyl)xanthine or 1-(n-propyl, isobutyl, n-hexyl or pentyl)-3-methyl-7-(5-hydroxyhexyl)xanthine.

3. The compound according to claim 2 which is 1-(5-hydroxyhexyl)-3-methyl-7-ethylxanthine.

4. A compound of the formula

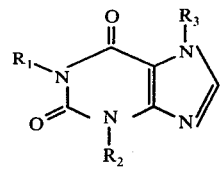

wherein
one of $R_1$, $R_2$ and $R_3$ is 5-hydroxyhexyl;
one of $R_1$, $R_2$ and $R_3$ is alkyl having from 2 to 12 carbon atoms; and
one of $R_1$, $R_2$ and $R_3$ is a hydrogen atom (—H) or alkyl having from 1 to 12 carbon atoms;
$R_2$ being alkyl or 5-hydroxyhexyl; or a physiologically-acceptable acid-addition salt of such compound.

5. A compound as claimed in claim 4 having an alkyl with more than 2 carbon atoms.

6. A compound as claimed in claim 4 wherein one of $R_1$, $R_2$ and $R_3$ is methyl.

7. A physiologically-acceptable acid-addition salt as claimed in claim 4.

8. A cerebral-blood-flow-improving pharmaceutical composition in which a pharmaceutical carrier or excipient is in association with an effective concentration of an essential active ingredient, which is a compound as claimed in claim 4 or a physiologically-acceptable acid-addition salt thereof.

9. A composition as claimed in claim 8 in a form suitable for oral administration.

10. A composition as claimed in claim 8 which additionally has a further active ingredient.

11. A composition as claimed in claim 8 in a form suitable for rectal or parenteral administration.

12. A method of improving cerebral blood circulation by administering to a person suffering from insufficiency of cerebral blood circulation an effective amount of a physiologically-acceptable compound or acid-addition salt as claimed in claim 4.

13. A compound of the formula

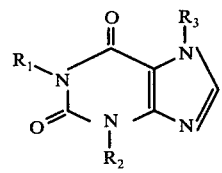

wherein
one of $R_1$, $R_2$ and $R_3$ is 6-hydroxyhexyl;
one of $R_1$, $R_2$ and $R_3$ is alkyl having from 2 to 12 carbon atoms; and
one of $R_1$, $R_2$ and $R_3$ is a hydrogen atom (—H) or alkyl having from 1 to 12 carbon atoms;
$R_2$ being alkyl or 6-hydroxyhexyl; or a physiologically-acceptable acid-addition salt of such compound.

14. A compound as claimed in claim 13 having an alkyl with more than 2 carbon atoms.

15. A compound as claimed in claim 13 wherein one of $R_1$, $R_2$ and $R_3$ is methyl.

16. A physiologically-acceptable acid-addition salt as claimed in claim 13.

17. A cerebral-blood-flow-improving pharmaceutical composition in which a pharmaceutical carrier or excipient is in association with an effective concentration of an essential active ingredient, which is a compound as claimed in claim 13 or a physiologically-acceptable acid-addition salt thereof.

18. A composition as claimed in claim 17 in a form suitable for oral administration.

19. A composition as claimed in claim 17 which additionally has a further active ingredient.

20. A composition as claimed in claim 17 in a form suitable for rectal or parenteral administration.

21. A method of improving cerebral blood circulation by administering to a person suffering from insufficiency of cerebral blood circulation an effective amount of a physiologically-acceptable compound or acid-addition salt as claimed in claim 13.

* * * * *